United States Patent [19]

Lee

[11] Patent Number: 5,665,104
[45] Date of Patent: Sep. 9, 1997

[54] BREATHING ENHANCER

[76] Inventor: Chi Hao Edwin Lee, 61 Twin Oaks Rd., Bridgewater, N.J. 08807

[21] Appl. No.: 700,213

[22] Filed: Aug. 20, 1996

[51] Int. Cl.$^6$ ................................ A61M 29/00
[52] U.S. Cl. ........................ 606/199; 128/200.24
[58] Field of Search ................ 606/199, 204.45, 606/196; 128/200.24; 604/43–45

[56] References Cited

U.S. PATENT DOCUMENTS

| | | | |
|---|---|---|---|
| 1,256,188 | 2/1918 | Wilson | 606/199 |
| 2,569,743 | 10/1951 | Carlock | 606/199 |
| 2,672,138 | 3/1954 | Carlock | 606/199 |
| 3,710,799 | 1/1973 | Caballero | 606/199 |

FOREIGN PATENT DOCUMENTS

| | | | |
|---|---|---|---|
| 0363758 | 8/1906 | France | 606/199 |
| 2260979 | 9/1975 | France | 606/199 |
| 266605 | 10/1913 | Germany | 606/199 |

*Primary Examiner*—Michael Buiz
*Assistant Examiner*—Nancy Connolly Mulcare
*Attorney, Agent, or Firm*—Thomas A. Beck

[57] ABSTRACT

A nasal dilator device comprising two molded, rigid, substantially cylindrical insert pieces fixed to each other by a connecting strip at the respective bases thereof. Each insert piece is inserted into a vestibule of the nose to expand the area of the nostril, thereby enhancing breathing.

2 Claims, 2 Drawing Sheets

BREATHING ENHANCER

BACKGROUND OF THE INVENTION

1. Technical Field of the Invention

The present invention relates generally to an article which is inserted into each nostril of the nose of a human being to increase the breathing space thereof. The article comprises two molded, rigid, substantially cylindrical pieces fixed to each other by a connecting strip at the respective bases thereof.

2. Description of the Related Art

There are breathing aids on the market that purport to enhance breathing. One product that is currently available is a nasal strip which consists of two plastic strips embedded in a single plastic material. The strip is adhered to the bridge of the nose causing each of the two plastic strips to straighten and force the nasal passages to open wider. This article is used externally and differs from the present invention in that it is not inserted within the nostrils. Accordingly, since the strip is used externally, the adhesive which adheres it to the nose may cause skin irritation. Further, when used during strenuous exercise, the sweat resulting from the exercise may cause the adhesive to lose its grip and the strip will loosen and not provide the result desired.

Another article is a U-shaped clip having substantially spherical members on each end thereof. Each of the spherical members presses against the septum nerves in the nostrils to enhance air flow. The spherical members stimulate the trigeminal. This stimulation action is said to dilate the nasal passages, thereby reducing snoring.

Another article used to enhance breathing is an arcuate shaped relatively flexible device made from a rigid material. The device consists of a connecting device having relatively blunt ends, each of which is inserted in one or both nostrils to enhance air flow. The arcuate shape of the article inserted in the nostrils serves to push the side of the nostril opposite the septum away from the septum outwardly, and thus widen the nasal cavity.

These articles do not appear to provide the desired result with all persons who use them and in some cases the breathing became more difficult.

SUMMARY OF THE INVENTION

The nose is the organ of olfaction and the entrance that warms, moistens and filters the air as it passes through en route to the respiratory tract. The external portion of the nose is a triangle of cartilage and bone covered with skin and lined in the interior with mucous membrane (mucosa).

Internally, a septum divides the nose into two chambers. Each chamber contains three meatus, which are found underneath the corresponding turbinated. Orifices of frontal, anterior, ethmoid and maxillary sinuses are in the middle meatus. Orifices of posterior ethmoids and sphenoids are in superior meatus.

The article of the present invention increases the efficiency of the human breathing process, especially when the user is engaged in physical exercise or sports. The article comprises two molded rigid substantially cylindrical members generally referred to herein as "dilators", each having a leading edge which is beveled or chamfered at the top thereof to allow ease of insertion into the nose chamber (vestibule), and a base. The dilators are adapted to be inserted in each of the vestibules separated the septum as described above. The leading edge of the dilators may be narrower than the base thus also aiding the insertion of the dilator into the vestibule. The shape of the dilators may follow generally the interior contour of the vestibule. When the members are in place in the vestibule, the vestibule is distended and breathing is thus made more efficient as there is a greater area available for the breathing process.

Using the laws of geometry to consider figures of various shapes whose sides are predetermined, so that all of the figures under consideration have perimeters of equal dimension, it is clear that a circle, as opposed to a rectangle, triangle, etc., yields the maximum area. To illustrate this point in the context of the present invention, a horizontal cross-section of the human nose (i.e. viewed from beneath the nostrils) bears a rough resemblance (for the sake of discussion) to an isosceles triangle. Assuming that the sides, measure 20 mm each, and the base connecting the sides measures 10 mm the total perimeter distance computed by adding the value of the sides, is 50 mm as depicted in FIG. 1. FIG. 2 is a circle having a circumference of 50 mm. The total perimeter of both figures is equal; that is, they both add up to 50 mm. However, if one computes the areas encompassed within the two figures, it is obvious that the circle encloses more than twice the space as is enclosed within the triangle. The normal configuration of human nostrils more closely resembles FIG. 1 rather than FIG. 2. If there is a means to change the area depicted in FIG. 1 to the area depicted in FIG. 2, and if that means for change is applied to a nose, the amount of air that can move in and out of the chambers and ultimately the respiratory system, will be doubled.

The dilators of the present invention, when inserted into nostrils, make changes on the order of that depicted in FIGS. 1 and 2. Thus, the cross sectional shape of the nostril chambers upon insertion of the articles of the present invention therein are changed from the general shape depicted in FIG. 1 to that depicted in FIG. 2.

By maximizing the breathing capacity, an athlete can greatly increase his or her endurance and performance. The article of the present invention may also help respiration in conditions such as an irregular septum, enlarged turbinates or other mechanical impedimentsto the free flow of air in and out of the nose. This device may also help people suffering from certain conditions like asthma, snoring, etc.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
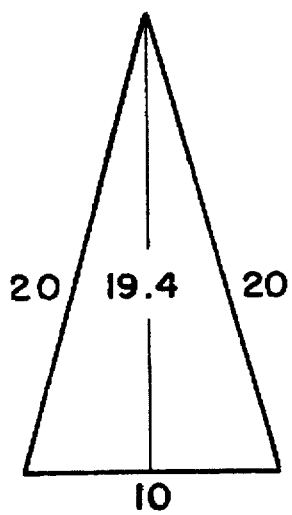
FIG. 1 is a diagram of an isosceles triangle showing perimeter dimensions of the base height and hypotenuse.
Figure 2:
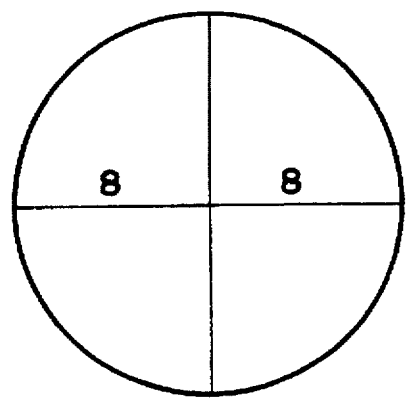
FIG. 2 is a diagram of a circle having the same perimeter as the triangle in FIG. 1.
Figure 3A:
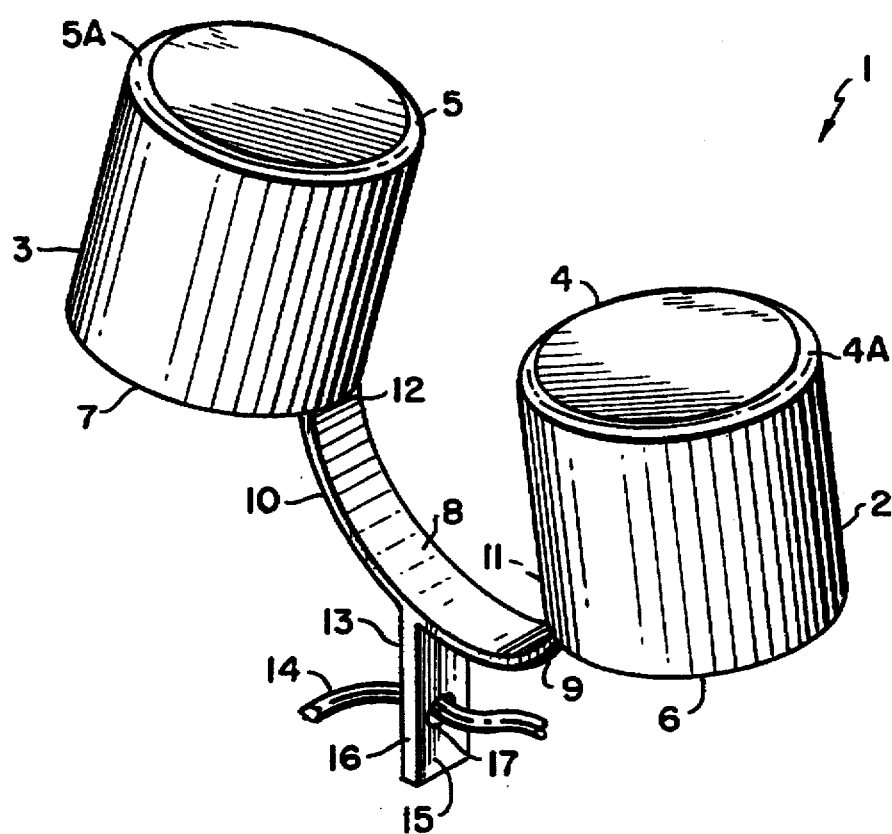
FIG. 3 is a front isometric view of the article of the present invention.
Figure 3:
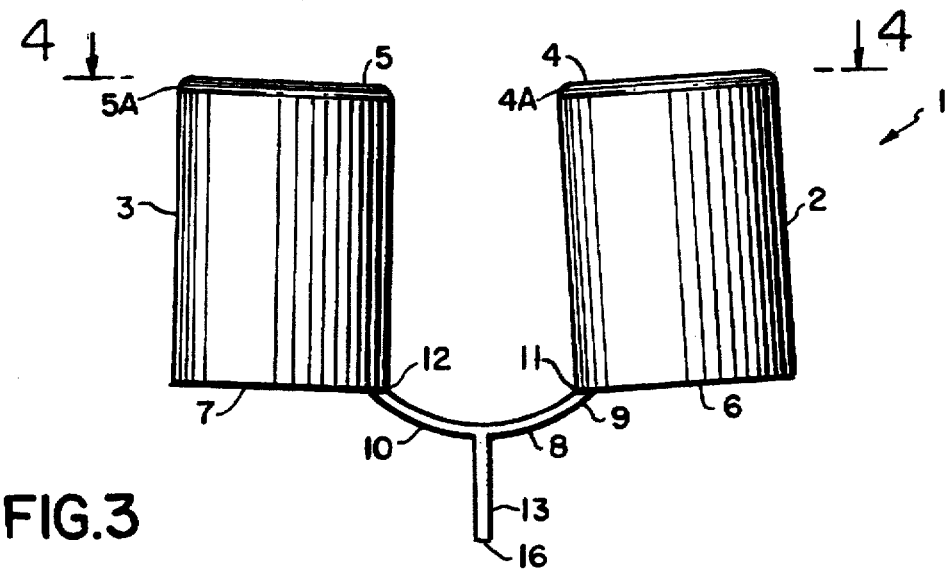

Referring to FIG. 3, the nasal dilator unit 1 of the present invention which serves as a breathing enhancing article comprises two molded, rigid substantially cylindrical dilators 2, 3 each having a leading edge top 4,5 which is the portion that penetrates furthest up the nostril chamber. Each dilator 2, 3 also has a base 6,7 respectively, each of which is substantially parallel to leading edges 4, 5. Leading edges 4, 5 are beveled or chamfered at 4A and 5A so as not to scrape or injure the mucosa in the nasal chambers when inserted into or removed from the nostril. The symmetry of members 2, 3 is shaped so as to conform in general with the shape of the nasal passages when inserted in place.

A centerpiece 8 has its ends 9 and 10 secured to base 6 or 7 of each of the dilators at intersections 11 and 12. Centerpiece 8 is preferably bent into a "U" shape when ends 9 and 10 are secured to dilators 2, 3. Centerpiece 8 has a concavity to fit the columella of the septum. Dilators 2, 3 may be secured to centerpiece 8 at 11, 12 using any convenient molding process. Preferably, dilators 2, 3 are secured to centerpiece 8 so that, at rest, when not in use, they slope toward each other. Because centerpiece 8 comprises a substantially rigid but flexible plastic, dilators 2, 3 can be spread apart from each other, however, when the bias separating each is released, because of the plastic memory of connector 8, they resume their original "at rest" orientation with respect to each other. This feature allows the dilator units to be held in place in the nostrils due to the inward force supplied by the plastic memory of connector 8. In this manner, the dilators are angled into the nostril and thus secure in the nasal passage via a "force fit."

Optionally, extending generally downward from connector 8 is anchoring strip 13 which allows the article to be secured to the user. Referring to FIG. 3, anchoring strip 13 has an opening 17 therethrough to receive means 14 for securing dilators 2, 3 into the nostrils of the wearer. The means may be a string, elastic band, chain, etc. which encircles the users head so that the article will be held in place and will not disengage itself from the nostrils. When in place, means 14 insures that dilators 2, 3 are held in place in the nostrils.

If desired, the orientation of anchor strip 13 can be changed 90° so that the width 15 (as opposed to the edge 16) of anchor strip 13 is adjacent or in contact with the area of the philtrum of the wearer. In the event anchor strip 13 is so oriented, the article can be retained in place by securing width 15 to the upper lip of the user by means of adhesive tape or any other suitable means to hold the unit in place.

To use the device of the present invention, a person simply inserts dilators 2, 3 up into the nostrils while simultaneously pushing until they fit snugly within the chamber.

The device of the present invention is made from any inert natural or synthetic material which can be formed into the necessary shape. It must be rigid enough to retain its shape when inserted into the nostril and must not irritate the mucosa of the nostril. Suitable materials may be any synthetic or natural materials that are FDA approved and are flesh colored.

Dilators are made in several sizes depending upon the size of the nose in which they are to be used.

The device of the present invention greatly increases the breathing space of the nose by: 1) transforming the nasal opening to the optimum configuration, namely, a circle; 2) expansion of the nasal walls outwardly as a result of the gently upward push of the robes; and 3) the rigid support of the tubes which internally prevents the collapsing of the nasal walls during forceful deep inhalation.

Figure 4:
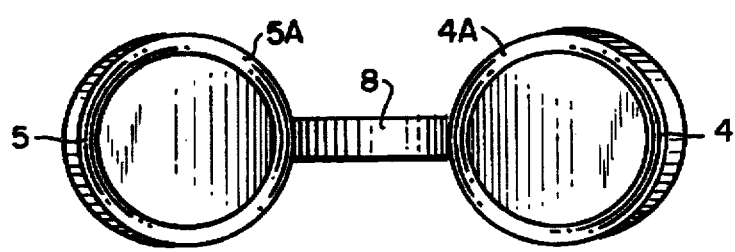
FIG. 4 is a top view of the article of the present invention.

FIG. 4 depicts a top view of the article depicted in FIG. 3 with chamfered edges 4A and 5A and further shows connecting means 8.

Figure 5:
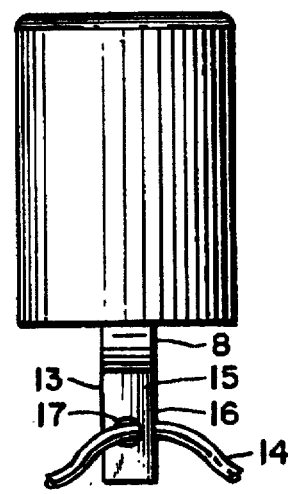
FIG. 5 is a side view of the article of the present invention.

FIG. 5 depicts a side view of the article depicted in FIG. 3 showing dilator 4 of the dilators with chamfered edges 4A as well as connecting strip 8 and anchor strip 13 means that joins dilators 2, 3, showing width 15 and edge 16 thereof and securing means 14 through opening 17.

The invention is not limited by the embodiments described above which are presented as examples only but can be modified in various ways within the scope of protection defined by the appended patent claims.

I claim:

1. A breathing enhancer made from substantially rigid natural or synthetic material, comprising a pair of cylindrical dilators, adapted to be inserted into the nasal cavity and positioned therein adjacent nasal walls in said nasal cavity, each said cylindrical dilator having an inside wall and an outside wall, a top connecting said inside and said outside walls, and a base;

each said inside wall having a height greater than the height of each said outside wall, so that said top connecting said inside wall and said outside wall has a chamfered appearance;

a substantially rigid "U" shaped center connecting piece extending between said base of each said cylindrical dilator;

each said dilator fixedly secured to said "U" shaped center connecting piece so that at rest, said dilators slope convergently inward toward each other;

each said dilator having a substantially uniform cross sectional area, and having a height sufficient to support with said nasal walls during forceful deep inhalation and to prevent said nasal wall from collapsing.

2. The breathing enhancer defined in claim 1 wherein an anchoring strip is suspended vertically from said "U" shaped connecting strip which is useable as a handle to insert said breathing enhancer into said nasal cavity.

* * * * *